United States Patent [19]

Williamson et al.

[11] 4,448,203

[45] May 15, 1984

[54] ELECTROMYOGRAPHIC DIAGNOSTIC DEVICE

[75] Inventors: Eugene Williamson, Evans, Ga.; Stephen M. Thompson; Derek K. Evans, both of San Diego, Calif.

[73] Assignee: "A" Company, San Diego, Calif.

[21] Appl. No.: 422,927

[22] Filed: Sep. 24, 1982

[51] Int. Cl.³ .............................................. A61B 5/04
[52] U.S. Cl. .................................................. 128/733
[58] Field of Search ....................... 128/733, 696–706, 128/419 PG, 419 D, 731

[56] References Cited

U.S. PATENT DOCUMENTS 3,905,355  9/1975  Brudny .
3,983,865 10/1976  Shepard .
4,359,724 11/1982  Zimmerman .

OTHER PUBLICATIONS

Yamada et al., "An Automated Measuring System for EMG Silent.," IEEE Transon Biomed Eng., vol. BME 27, No. 7, Jul. 1980.
Gigauri et al., Biomed Eng., vol. 8, No. 4, Jul.–Aug. 1974, p. 232–234 "Instr. for Automatic Monitoring of Muscle Relaxation of a Patient".

Primary Examiner—Kyle L. Howell
Assistant Examiner—Deidre A. Foley
Attorney, Agent, or Firm—Townsend and Townsend

[57] ABSTRACT

An inexpensive apparatus for sensing and displaying the duration of the Silent Periods of masticatory muscles, which is suitable for diagnostic applications made in a doctor's office. The apparatus includes electrode means to be applied to the skin overlying a masticatory muscle and for sensing electrical activity within the muscle, and means providing an electrical signal representative of the sensed electrical activity. The apparatus further includes means receiving the representative electrical signal and sensing therein the onset of a Silent Period. Further means rejects those Silent Periods which have a duration less than a predetermined time interval, which time interval is selected to establish a minimum Silent Period of interest. Finally, the apparatus determines and displays the duration only of those Silent Periods longer than the predetermined time interval.

11 Claims, 3 Drawing Figures

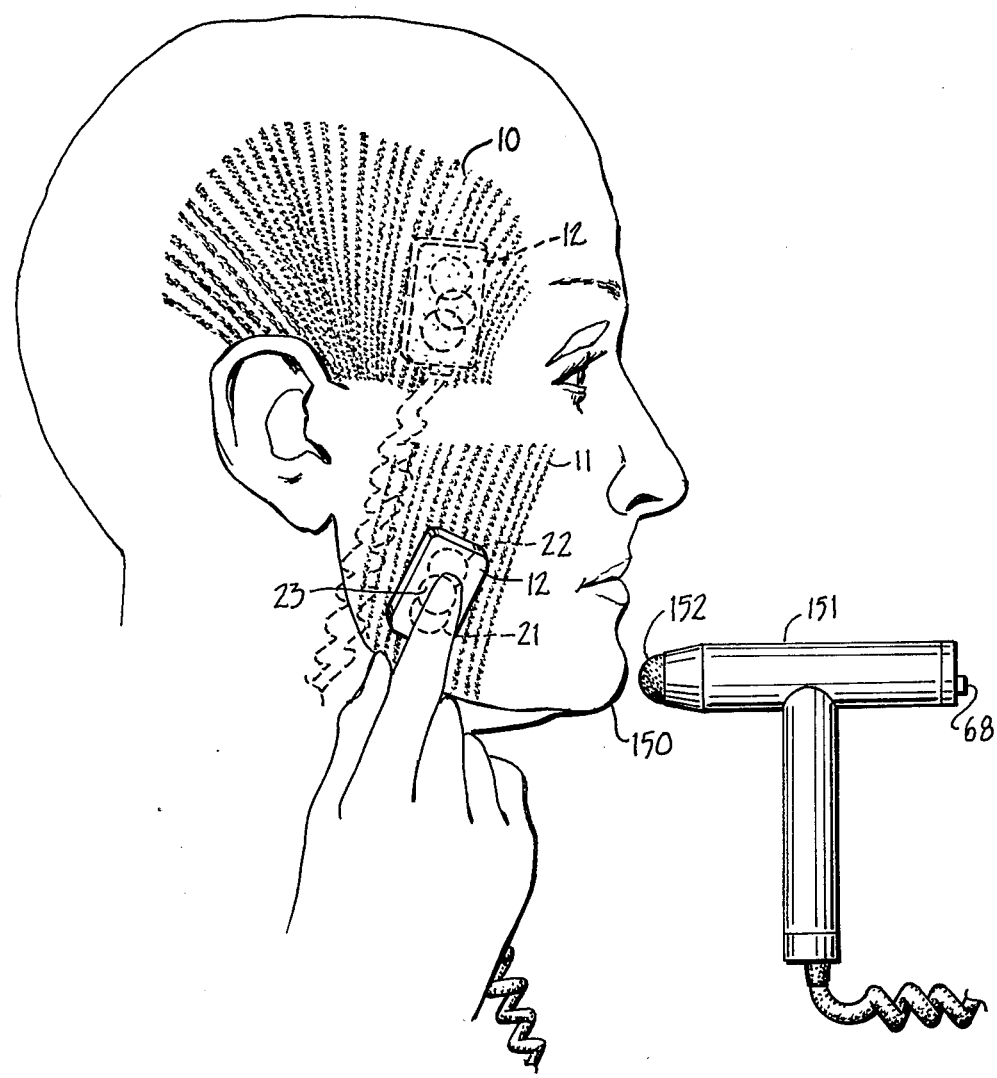
FIG._1.

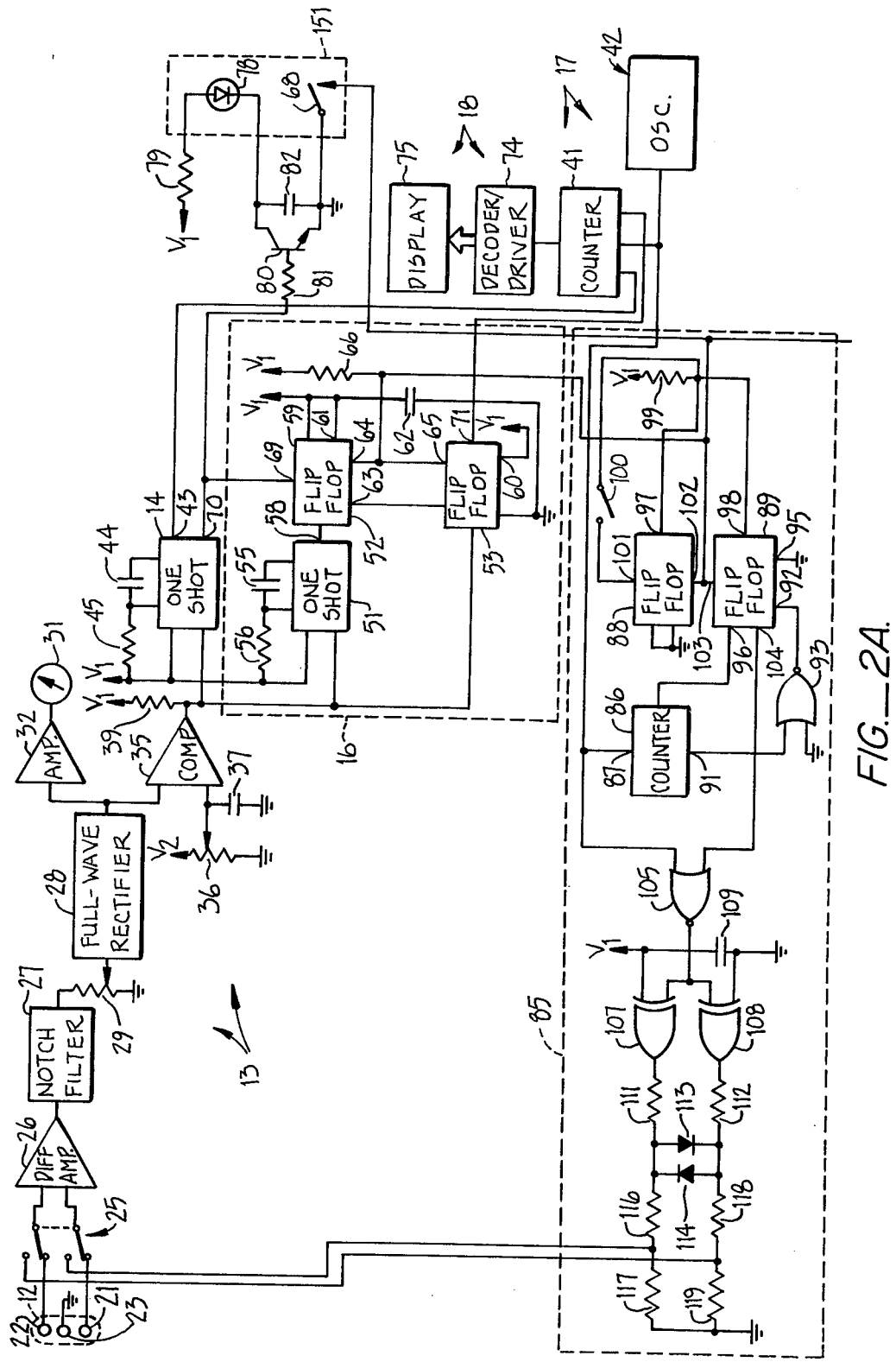
FIG._2A.

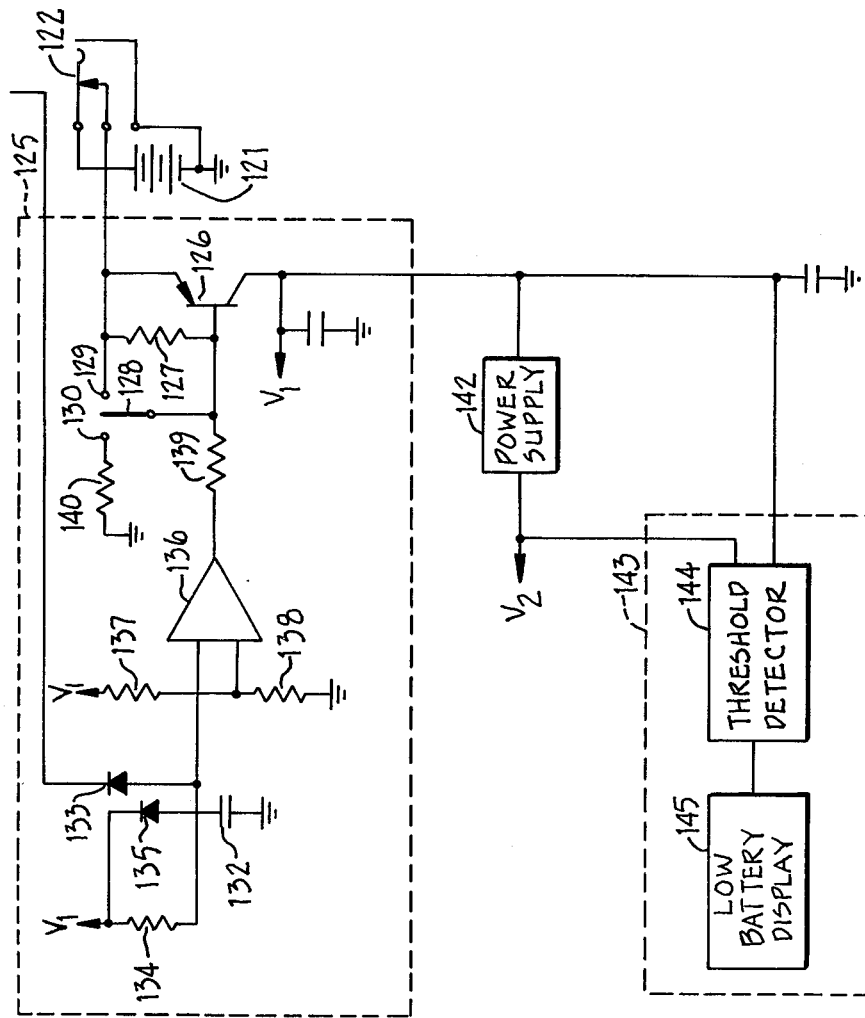

ELECTROMYOGRAPHIC DIAGNOSTIC DEVICE

BACKGROUND OF THE INVENTION

The invention relates generally to the field of electromyography and is more particularly directed to means for the clinical detection and indication of abnormal electromyographic response of the masticatory muscles.

Electromyography is concerned with the measurement of electrical signals which accompany skeletal muscle activity. Laboratory apparatus for detecting and recording these signals has been available to medical researchers for some time and has enabled them to gain insight into the etiology of various neuromuscular disorders. Electromyography also shows promise as a useful clinical tool in the diagnosis and treatment of certain neuromuscular disorders.

In particular, certain jaw disorders are known to affect the electrical activity of the masticatory muscles. In the muscles spanning the temple area and the upper reaches of the jaw—the temporalis and masseter—an electrical signal is generated when a person clenches the teeth. It is a well documented phenomenon that when the masticatory muscles are contracted in this way and the chin is tapped lightly, there will be a momentary cessation of electrical activity. This momentary cessation is known as the Silent Period.

The studies of Bessette and Shatkin, *Journal of Plastic Reconstructive Surgery*, Vol. 64, pp. 232–238, and of Skiba and Laskin, *Journal of Dental Research*, Vol. 60, pp. 699–706, among others, have shown that persons with temporomandibular joint dysfunction or myofascial pain dysfunction exhibit prolonged Silent Periods. Moreover, the degree of prolongation appears to be directly related to the severity of the symptoms.

These studies suggest that measurement of the Silent Period could be a useful tool for the clinician in the diagnosis and treatment of the above-mentioned disorders, to be used along with such other established modalities as muscle palpation, maximum jaw opening, and the patient's own subjective symptoms.

Although the Silent Period has been referred to as though a well defined quantity, this represents an idealization. In fact a typical electromyographic waveform displays erratic spikes and fluctuations. Short periods of reduced electrical signal interspersed between the spikes can be confused with true Silent Periods associated with reflexive muscle response. Moreover, even true Silent Periods do not always have a clearly delineated beginning, but rather sometimes follow upon the tail of a gradually decaying waveform from a peak of electrical activity. And as with any other weak electrical signal, noise interference will sometimes obscure important features. Experienced researchers will be able to recognize features of significance in a complex electromyographic waveform, but the typical clinician will not have the requisite interpretive training to apply electromyographic analysis as a reliable diagnostic tool.

Moreover, known electromyographic apparatus used in medical research is generally too expensive and too impractical to find widespread use in clinical applications. An attempt to develop an instrument more suitable for clinical use has been made by Yamada et al., *IEEE Transactions on Biomedical Engineering*, Vol. BME-27, No. 7 (July 1980). Although their instrument shows a great simplification over laboratory electromyographic apparatus, it is still more complicated than need be. The Yamada instrument measures both the duration and latency of the Silent Period. "Latency" is understood to mean that period of time between application of the inducing stimulus and the onset of the Silent Period. To measure latency, the Yamada instrument includes a memory module for "memorizing" a digital data stream representative of electrical activity. The data may then be retrieved to display the history of the electrical activity over the 60-ms period following the inducing stimulus. Yamada, et al display this history in a pictorial fashion by a series of light-emitting diodes, which are individually either turned on or off to correspond to the relative presence or absence of electrical activity in a 2-ms interval.

While the Yamada device represents a practical improvement over laboratory instrumentation, it is unnecessarily complicated and still calls for interpretive skill in understanding the displayed waveform. Moreover, certain muscle and jaw disorders can be diagnosed on the basis of Silent Period measurement without simultaneous latency measurement. Clinicians interested only in such applications have no need for the extra capabilities and concomitant complications of the Yamada instrument.

The success of an electromyographic device as a diagnostic tool in a private medical or dental office depends on its cost and simplicity of operation. The lower the cost of the instrument and the easier it can be applied, the lower will be the expense to the patient.

SUMMARY OF THE INVENTION

The invention provides an inexpensive clinical apparatus for sensing and displaying the duration of masticatory muscle Silent Periods suitable for diagnostic applications in a doctor's office. Apparatus embodying the invention will operate according to the following method, which initially calls for sensing electrical activity of a masticatory muscle and measuring off a predetermined time interval whenever the sensed electrical activity falls below a predetermined level. Activity below the predetermined level is indicative of the onset of a period of reduced signal which could possibly be a Silent Period associated with a reflexive muscle response. The predetermined time interval represents a minimum cutoff Silent Period of interest for diagnostic purposes. The method then calls for rejecting those "Silent Periods" terminating before the predetermined time interval, that is, false Silent Periods, while measuring and displaying the durations of Silent Periods terminating after the predetermined time interval.

Apparatus for sensing Silent Periods by means of the above method comprises electrode means for sensing electrical activity of a masticatory muscle, means connected to the electrode means and providing an electrical signal representative of the sensed electrical activity, means receiving the representative electrical signal for sensing the onset of a period of reduced electrical activity, means receiving the representative electrical signal and rejecting any Silent Period having a duration less than a predetermined time interval, means for determining the duration of any Silent Period longer than the predetermined time interval, and means for displaying the duration of any Silent Period so determined. Strictly speaking, the term Silent Period refers to a reflexive pause in the electrical activity of a contracted muscle induced by mechanical stimulation of the muscle. However, it will be convenient from time to time to use the term more loosely to refer to any pause in electrical activity or to any significant reduction in electrical signal level, no matter what the cause. Where confusion could arise, the terms true Silent Period and false Silent Period will be used, respectively, to distinguish those pauses associated with reflexive muscle response from those having other causes.

In the preferred embodiment, the means for rejecting Silent Periods having unacceptably short durations will generally include delay means for defining the predetermined time interval. The delay means starts to measure off the time interval each time the representative electrical signal drops below the minimum predetermined level of activity. The duration of a Silent Period is recorded only if the Silent Period terminates after the delay means has finished measuring off the predetermined time interval.

The diagnostic apparatus of the present invention can advantageously be fabricated in a lightweight, portable, and inexpensive instrument, making it affordable for doctors having small practices. Thus, the present invention offers the advantage that it is within the economic reach of a large number of practitioners and is not limited by its cost to use only in hospitals or large clinics.

The invention has the further advantage that it is particularly simple to operate and displays only the information of immediate concern to the clinician in diagnosing the presence of masticatory muscle dysfunction. With the present invention the clinician is not called upon to make an intermediate interpretation of the masticatory electromyographic response signal.

A further understanding and appreciation of the nature and advantages of the invention will be gained by reference to the remaining portion of the specification and to the attached drawings.

BRIEF DESCRIPTION OF THE DRAWINGS

FIG. 1 is a pictorial representation of a human profile showing the proper application of electrode means to the masticatory muscle for practicing the invention.

FIG. 2 is composed of FIGS. 2A and 2B, which taken together provide a schematic block diagram of a diagnostic device constructed in accordance with the invention.

DETAILED DESCRIPTION OF PREFERRED EMBODIMENTS

FIG. 1 shows the temporalis and masseter muscles 10 and 11, respectively, which are known to exhibit abnormal Silent Periods as a result of various physical or emotional etiologies. The Silent Period of the masseter muscle normally lies in the range of 15 to 35 milliseconds. That of the temporalis normally lies in the range of 16 to 25 milliseconds. In patients manifesting temporomandibular joint dysfunction (TMJ) or myofascial pain syndrome (MPS) the Silent Periods of these muscles are observed to exceed 38 and 26 milliseconds, respectively, the amount of prolongation being related to the severity of the symptoms. The present invention is adapted to function specifically with these muscles and to give an estimate of the Silent Period of sufficient accuracy for use in diagnosing and monitoring the treatment of such disorders as TMJ and MPS.

Apparatus constructed in accordance with the invention is illustrated in the schematic diagram of FIG. 2. The apparatus comprises electrode means 12 for sensing electrical activity of masticatory muscles 10 or 11, means indicated generally at 13 for providing an electrical signal representative of the sensed electrical activity, means 14 for sensing the onset of a period of reduced electrical activity (indicating a possible Silent Period of interest), means 16 for rejecting false Silent Periods (that is, periods of reduced electrical activity having a duration too short to be of interest), means 17 for determining the approximate duration of any Silent Period of interest, and means 18 for displaying the duration so determined.

The electrical activity of the masticatory muscles will manifest itself in a weak signal having a fundamental frequency of roughly 12 kilohertz. Electrode means 12 includes electrodes 21, 22, and 23. Electrodes 21 and 22 are adapted to be applied to the skin overlying muscle 10 or 11 for sensing the weak signal therein. They are preferably formed to engage the skin over the area of a disc so as to provide good electrical contact and are spaced apart by roughly one inch. Electrode 23 is connected to the common ground of the remaining portions of the apparatus. Electrode 23 is disposed on the opposite side of means 12 from electrode 21 and 22 so that in application the patient may place his or her index finger on electrode 23 while applying electrodes 21 and 22 to the skin. In this manner the instrument will be grounded to the patient so as to prevent shock.

Means 13 providing a representative electrical signal receives the signals sensed by electrodes 21 and 22 through double-pole-double-throw switch 25. The extremely weak signals sensed by electrodes 21 and 22 are first pre- amplified by differential amplifier 26 having a gain of roughly 1,000. As will be readily understood by those skilled in the art, pre-amp 26 will preferably be a compensated amplifier having a standard rolloff network for the frequencies being amplified. The output signal from pre-amp 26 is fed to passive notch filter 27 for removing 60-hertz interference. Notch filter 27 may be provided by a conventional twin-T filter circuit.

In the preferred embodiment the output signal from notch filter 27 is fed to a balanced precision full-wave rectifier 28. Interposed between filter 27 and rectifier 28 is a gain control, represented symbolically by potentiometer 29. The output signal from rectifier 28 is fed to meter 31 through drive amplifier 32. Meter 31 displays the mean amplitude of the rectified signal. Although a drive amplifier 32 is shown in FIG. 2A, meter 31 can also be driven conveniently by a current follower circuit incorporated in the output stage of rectifier 28.

The output signal from rectifier 28 is also fed to one input of threshold comparator 35. Comparator 35 has a reference level, which can be set in conventional manner by the level adjust circuit feeding the second input of comparator 35 and comprising potentiometer 36 and capacitor 37. Comparator 35 will then provide an output signal having two levels, a first level whenever the amplified and rectified signal has a magnitude less than the comparator reference level, and a second level otherwise. In particular, because rectifier 28 provides full-wave rectification, every zero crossing of the sensed electrical activity will provide a corresponding shift between the two levels of the comparator output signal. When the muscle under examination exhibits a Silent Period, the output signal from comparator 35 remains in its first level for the duration of the Silent Period. Thus, the output signal of comparator 35 provides a representation of the muscle electrical activity particularly convenient for determination of Silent Period durations.

Other, equivalent circuits may be employed to provide the same, or an equally suitable, representative signal. For example, a dual threshold comparator can be used in place of comparator 35 and rectifier 28. However, the embodiment of FIG. 2A is convenient because the sensed electrical signal must in any event be rectified to drive meter 31.

In a preferred embodiment means 14 for sensing the onset of a Silent Period is provided by a monostable multivibrator (one-shot). One side of a 96L02 dual monostable multivibrator is suitable for this purpose. The output signal from comparator 35 communicates with a first input of one-shot 14, which input communicates with the bias potential $V_1$, through pullup resistor 39. The 96L02 one-shot is provided with two inputs for triggering by either high-to-low or low-to-high transitions. In the embodiment of FIG. 2A the inputs are biased so that the one-shot will be triggered by a high-to-low transition, that is, by a negative-going pulse.

Means 17 for determining the duration of a Silent Period is provided by counter 41 driven by oscillator 42. A one-kilohertz oscillator has been found suitable for the time scales involved. The complementary Q output 33 of one-shot 14 communicates with the reset input of counter 41 to provide a count-initiating pulse. The pulse width of one-shot 14 is determined by the values of capacitor 44 and resistor 45. In practice one-shot 14 need have only a very short pulse width, say, one microsecond, as required to reset counter 41.

Thus, counter 41 will be reset and will start to count with each transition of the comparator output signal from its high level to its low level. That is, the counter will be reset whenever the unrectified wave form detected by electrode means 12 falls below a fixed magnitude substantially less than the peak magnitude and determined by the gain setting (potentiometer 29) and comparator reference level (potentiometer 36). This will occur at the onset of a true Silent Period, but will also occur with every zero crossing of the unrectified signal as well as with other momentary erratic reductions in electrical activity due to statistical fluctuations or other causes. Although such momentary reductions in the electrical signal below the reference level of comparator 35 will start counter 41, these events do not represent the onset of true Silent Periods. These events are automatically rejected in the present invention by means 16.

Means 16 comprises delay means 51 and D-type flip flops 52 and 53. In the preferred embodiment delay means 51 is provided by a monostable multivibrator, and in particular by the second side of the 96L02 integrated circuit component supplying multivibrator 14. As for one-shot 14, the inputs to one-shot 51 are biased so that one-shot 51 will be triggered by a negative-going pulse from comparator 35.

The width of the pulse generated by one-shot 51 defines a predetermined time interval which establishes the minimum Silent Period of interest. As explained more fully hereinbelow, cessation of electrical activity lasting for a period longer than the pulse width defined by one-shot 51 will be measured by counter 41. A relative absence of electrical activity for a period shorter than that defined by one-shot 51 will be considered to be a false Silent Period and will not be measured by counter 51. The pulse width of one-shot 51 is determined by the values of capacitor 55 and resistor 56. As a normal Silent Period is 15 to 35 milliseconds in duration, these values may be conveniently selected to give a pulse width of 8 to 10 milliseconds.

Flip flops 52 and 53 may be provided by a 74LS74 dual D-type flip flop integrated circuit. The complementary Q output 58 of one-shot 51 provides the clock input to flip flop 52. The clock input to flip flop 53 is provided by the output signal directly from comparator 35. The set and reset inputs on these flip flops are active-low inputs. The set inputs 59 and 60 of flip flops 52 and 53, respectively, are tied high along with the data input 61 to flip flop 52 and capacitor 62 provides a filter. The Q output 63 of flip flop 52 provides the data input to flip flop 53. The reset inputs 64 and 65 of flip flops 52 and 53, respectively, are tied together and to the $V_1$, bias supply through pullup resistor 66. Reset inputs 64 and 65 may be set by push- button switch 68. The complementary Q output 69 of flip flop 52 is connected to the clear input 70 of one-shot 14. The complementary Q output 71 supplies a count-terminating signal to the inhibit input of counter 41.

Counter 41 provides a signal indicative of the duration of a true Silent Period lasting longer than the predetermined time interval defined by one-shot 51. In a conventional manner means 18 displays the time period determined by counter 41. Means 18 may comprise a conventional decoder/driver 74 and liquid crystal display 75.

Light-emitting diode (LED) 78 indicates that the apparatus has been reset by the closing of switch 68. LED 78 is connected to the bias potential through resistor 79. Transistor 80, resistor 81, and filtering capacitor 82 provide a switch, activated by the complementary Q output 69 of flip flop 52, for energizing LED 78.

The present invention is intended for use in diagnosing the existence of potentially serious medical conditions. For the diagnosis to be reliable, it is essential that the device be in proper working order. For this reason the preferred embodiment will include test means 85 for providing an operational test of the device preliminary to its use in diagnosis. Test means 85 provides a test signal having a representative Silent Period of known duration, which is converted to a differential signal of small amplitude comparable to that sensed by electrode means 12. Switch 25 selectively applies either the test signal from test means 85 or the sensed signal from electrode means 12 to the inputs of preamp 26.

Test means 85 includes an eight-bit binary ripple counter 86 which generates a simulated Silent Period 256 counts in duration. The two sides of a 74LS393 dual four- bit ripple counter may be connected in series to provide counter 86. Counter 86 is reset and the remaining portion of the test circuit is gated by D-type flip flops 88 and 89. These flip flops are preferably provided by the two sides of a 74LS74 dual flip flop. The final Q output 91 of counter 86 communicates with the clock input 92 of flip flop 89 through NOR gate 93, the other input to NOR gate 93 being tied low. The data input 95 of flip flop 89 is similarly tied low. The complementary Q output 96 of flip flop 89 provides a reset signal to counter 86. The set inputs 97 and 98 of flip flops 88 and 89, respectively, are connected to $V_1$ through pullup resistor 99. Test means 85 is activated by switch 100, which connects Q output 101 of flip flop 88 to the low side of pullup resistor 99 and the set inputs 97 and 98. The reset inputs 102 and 103 of flip flops 88 and 89, respectively, are simultaneously activated by reset switch 68.

When reset switch 68 is closed and test switch 100 is then closed, counter 86 will be reset. After 256 counts a clock pulse will be applied to flip flop 89, which transfers the logic 0 at data input 95 to the Q output 104, which communicates with one input of NOR gate 105. Oscillator 42 communicates with the other input of NOR gate 105. Exclusive NOR gates 107 and 108 function as a square-wave pulse generator, gated by NOR gate 105 and with pulse width controlled by counter 86. Capacitor 109 provides for filtering. Gates 107 and 108 are followed by a wave-shaping circuit comprising resistors 111 and 112 and diodes 113 and 114. Resistor pair 116 and 117 and resistor pair 118 and 119 comprise voltage dividers to assure a test signal of the appropriate magnitude.

In the preferred embodiment of the invention the device is powered by battery 121. Jack 122 is provided for recharging the battery. As a safety precaution jack 122 includes an isolation switch whereby the device will automatically be disconnected and inoperable while the battery is being charged. Thus, there is no possibility of damage to the instrument or of shock to the patient if the device should inadvertently be applied to a patient while the battery is being charged.

To preserve battery 121, the device includes means 125 for automatically shutting the device off if it has not been used for a predetermined period. Transistor 126 and bias resistor 127 function as a switch for activating the device. When switch 128 engages contact 129, the device will be disconnected from the battery. When switch 128 engages contact 130, the device will be operative. When reset switch 68 is closed, capacitor 132 discharges to ground through diode 133. The voltage divider network comprising capacitor 132, resistor 134, and diode 135 begins to charge capacitor 132. The time constant of this network determines the automatic shut-off period of the device. A time constant on the order of 5 minutes is found to be convenient. Capacitor 132 communicates with one input of threshold detector 136. Resistors 137 and 138 comprise a voltage divider communicating with the other input of threshold detector 136. So long as switch 68 is not closed to reset the device in preparation for another diagnostic run, then capacitor 132 will continue to charge until threshold detector 136 is tripped. The output signal from detector 136 is applied to the base of transistor 126 through a voltage divider comprised of resistors 139 and 140. Transistor 126 then shuts off to disconnect battery 121.

The digital circuitry will conventionally call for a five-volt supply voltage, indicated herein by $V_1$. In the preferred embodiment described herein means 13 is provided by analog circuitry, which will conventionally call for a higher supply voltage indicated herein by $V_2$. Thus, the device includes power supply 142, which converts the digital supply voltage $V_1$ to the appropriate analog supply voltage $V_2$.

As a proper supply voltage is necessary for reliable operation of the logic circuitry, the preferred embodiment will include a low-battery indicator 143 comprised in conventional manner of threshold detector 144 and display means 145 for indicating when the battery has become unacceptably low.

In operation, the following steps are followed to make a diagnostic run. First, the patient's skin is scrubbed with alcohol to remove any oil or dirt from the region to which the electrodes are to be applied. Then a light coating of conductivity gel is applied to electrodes 21, 22, and 23, taking care not to create a conducting path connecting the electrodes. Electrodes 21 and 22 are then applied to the skin overlying the muscle being examined. For the masseter muscle 11 the electrodes should be oriented with their direction of separation aligned with the long axis of the muscle fibers as shown in FIG. 1. For the temporalis muscle 10 the electrodes should be applied at a position just posterior to the frontal process of the zygomatic bone and the zygomatic process of the frontal bone. In holding electrode means 12 in position, the patient should place a finger on electrode 23 for common grounding with the instrument.

The patient then clenches his or her teeth so as to flex the muscles. While the muscles are in flexed condition, the operator adjusts potentiometer 29 to set the gain at a predetermined level indicated on meter 31. This adjustment serves to calibrate the device to the individual patient's level of electrical activity to assure proper tripping of comparator 35. The operator then closes switch 68 causing counter 41 and flip flops 52 and 53 to reset.

At this stage electrode means 12 will sense the normal electrical activity of the stressed muscles with no true Silent Periods. Counter 41 will be continually reset with every zero crossing of the electrical signal detected. No Silent Period will be displayed by means 18 because no period of reduced electrical signal should last longer than the predetermined time interval defined by one-shot 51.

The device is now ready for a diagnostic run. Once again the patient clenches his or her teeth to flex the masticatory muscles. The operator provides an abrupt mechanical stimulation of the muscle being examined so as to induce a Silent Period. This is most conveniently done by tapping the patient lightly on chin 150. Although any means may be used for tapping the patient on the chin, the preferred embodiment of the invention includes a mallet 151 having a rubber tip 152 for this purpose. Also for the convenience of the operator reset switch 68 and LED 78 are housed within mallet 151. This location of switch 68 and LED 78 is only for ease of resetting the device for repeated diagnostic runs and plays no functional role in the electronic performance of the circuitry.

The Silent Period induced by the tapping will be displayed on the liquid crystal display 75 until the device is reset by the operator.

In summary, the device disclosed herein measures only the information which the clinician needs for proper diagnosis of temporomandibular joint dysfunction, myofascial pain syndrome, and similar disorders. The clinician is not called upon to interpret a complex electromyographic wave form. Indeed, the clinician need not even have any special understanding of electromyography. The device disclosed herein can be fabricated of inexpensive standard integrated circuit components, bringing it within the budget of even sole practitioners.

While the above provides a full and complete disclosure of the preferred embodiment of the invention, various modifications, alternate constructions, and equivalents may be employed without departing from the true spirit and scope of the invention. For example, those skilled in the art will appreciate that other signal forms could be produced to represent the sensed electrical activity. Similarly, other digital circuitry well within the understanding of those skilled in the art could be employed to sense the onset of a Silent Period or to define a cutoff time interval establishing the minimum Silent Period to be measured. Therefore, the above description and illustrations should not be construed as limiting the scope of the invention, which is defined by the appended claims.

What is claimed is:

1. Apparatus for sensing the Silent Period of masticatory muscles comprising:
   electrode means adapted for contact with the skin overlying a masticatory muscle for sensing electrical activity of said muscle;
   first means connected to said electrode means and providing an electrical signal representative of the sensed electrical activity;
   second means receiving said representative electrical signal for sensing the onset of a Silent Period;
   third means receiving said representative electrical signal and communicating with said second means for rejecting a Silent Period having a duration less than a predetermined time interval;
   fourth means communicating with said second means and said third means for determining the duration of any Silent Period longer than said predetermined time interval; and
   display means for indicating the duration of any such Silent Period so determined.

2. The apparatus of claim 1, wherein said third means includes delay means for defining said predetermined time interval, said delay means providing a cutoff signal after the onset sensed by said second means delayed by said predetermined time interval.

3. The apparatus of claim 2, wherein said third means further includes means receiving said cutoff signal and providing a termination signal when a sensed Silent Period is longer than said predetermined time interval.

4. The apparatus of claim 3, wherein said fourth means comprises counter means for determining the interval between the onset of a Silent Period and said termination signal.

5. The apparatus of claim 1, further comprising test means providing a test signal having a representative Silent Period, and means for selectively applying one of said test means and said electrode means to said first means.

6. Apparatus for sensing the Silent Period of masticatory muscles comprising:
   electrode means adapted for contact with the skin overlying a masticatory muscle and sensing electrical activity of said muscle;
   first means connected to said electrode means and providing an electrical signal representative of the sensed electrical activity;
   counter means providing a signal indicative of the duration of a sensed Silent Period;
   second means receiving said representative electrical signal and supplying a count-initiating signal to said counter means when said representative electrical signal falls below a predetermined level;
   means receiving said representative electrical signal and providing a cutoff signal delayed a predetermined time interval after said count-initiating signal, said predetermined time interval defining a cutoff Silent Period;
   means receiving said representative electrical signal and said cutoff signal and supplying a count-terminating signal to said counter means when a sensed Silent Period is longer than said cutoff Silent Period; and
   display means receiving said signal indicative of duration from said counter means when a count has been terminated and displaying said duration.

7. The apparatus of claim 6, wherein said first means comprises a comparator having a reference level defined by said predetermined level, said comparator providing an output signal having a first level when the sensed electrical activity is less in magnitude than a predetermined amount and having a second level otherwise; and
   said second means comprises a monostable multivibrator receiving said comparator output signal, said multivibrator being triggered by the onset of said first level to provide said count-initiating signal 8. The apparatus of claim 6, further comprising test means providing a test signal having a representative Silent Period, and means for selectively applying one of said test means and said electrode means to said first means.

9. Apparatus for sensing the Silent Period of masticatory muscles comprising:
   electrode means adapted for contact with the skin overlying a masticatory muscle and sensing electrical activity of said muscle;
   a comparator connected to said electrode means and responsive to said sensed electrical activity said comparator having a predetermined reference level and providing a signal at an output thereof having a first level when the sensed electrical activity is less in magnitude than a predetermined amount and having a second level otherwise;
   counter means for determining the duration of a sensed Silent Period and providing a signal indicative thereof;
   a first monostable multivibrator receiving said comparator output signal and supplying a count-initiating signal to said counter means, said first multivibrator being triggered to supply said count-initiating signal by the onset of said first level;
   a second monostable multivibrator receiving said comparator output signal and providing a cutoff signal defining a cutoff Silent Period, said second multivibrator being triggered by the onset of said first level and providing said cutoff signal a predetermined time interval thereafter;
   means receiving said comparator output signal and said cutoff signal and supplying a count-terminating signal to said counter means whenever a sensed Silent Period is longer than said cutoff Silent Period; and
   display means receiving said signal provided by said counter means and displaying the duration of a sensed Silent Period longer than said cutoff Silent Period.

10. A method of sensing Silent Periods of masticatory muscles comprising the steps of:
    sensing electrical activity of a masticatory muscle;
    automatically measuring off a predetermined time interval whenever the sensed electrical activity falls below a predetermined level indicative of the onset of a Silent Period;
    automatically rejecting false Silent Periods terminating before said predetermined time interval; and
    measuring and displaying the duration of true Silent Periods terminating after said predetermined time interval.

11. A method of sensing Silent Periods of masticatory muscles comprising the steps of:
    sensing electrical activity of a masticatory muscle;

starting a counter when the sensed electrical activity falls below a predetermined level;

measuring off a predetermined time interval from the start of said counter, said time interval defining a cutoff Silent Period;

inhibiting said counter when the sensed electrical activity rises above said predetermined level after said predetermined time interval has elapsed;

resetting said counter when the sensed electrical activity rises above said predetermined level before said predetermined time interval has elapsed; and displaying the duration of a sensed Silent Period when said counter is inhibited after said cutoff Silent Period.

* * * * *